United States Patent
Broyden et al.

(10) Patent No.: US 11,436,910 B2
(45) Date of Patent: Sep. 6, 2022

(54) SYSTEM AND METHOD FOR HAND HYGIENE COMPLIANCE

(71) Applicant: WashURHands LLC, Blacksburg, VA (US)

(72) Inventors: Lisa Miller Broyden, Blacksburg, VA (US); Thomas William Weeks, Blacksburg, VA (US); Richard Marion Mansell, Covington, VA (US); Henry M. Bass, Blacksburg, VA (US)

(73) Assignee: WashURHands, LLC, Blacksburg, VA (US)

( * ) Notice: Subject to any disclaimer, the term of this patent is extended or adjusted under 35 U.S.C. 154(b) by 0 days.

(21) Appl. No.: 17/228,735

(22) Filed: Apr. 13, 2021

(65) Prior Publication Data

US 2022/0157152 A1    May 19, 2022

Related U.S. Application Data

(60) Provisional application No. 63/101,012, filed on Apr. 13, 2020.

(51) Int. Cl.
*G08B 1/08* (2006.01)
*G08B 21/24* (2006.01)

(52) U.S. Cl.
CPC ................. *G08B 21/245* (2013.01)

(58) Field of Classification Search
CPC .......... G08B 21/245; G06K 9/00355
See application file for complete search history.

(56) References Cited

U.S. PATENT DOCUMENTS

| | | | |
|---|---|---|---|
| 6,125,482 A * | 10/2000 | Foster | E03C 1/057 4/628 |
| 7,551,092 B1 | 6/2009 | Henry | |
| 8,237,558 B2 * | 8/2012 | Seyed Momen | G08B 21/245 340/286.07 |
| 9,911,312 B2 | 3/2018 | Wildman et al. | |
| 9,922,534 B2 | 3/2018 | Gaisser et al. | |
| 10,102,735 B2 | 10/2018 | Easter | |
| 10,282,969 B2 | 5/2019 | Hermann et al. | |
| 10,403,121 B2 | 9/2019 | Liu et al. | |
| 10,438,476 B2 | 10/2019 | Sengstaken, Jr. | |
| 10,818,157 B1 * | 10/2020 | Koester | B05B 12/004 |
| 2007/0096930 A1 | 5/2007 | Cardoso | |
| 2010/0073162 A1 * | 3/2010 | Johnson | G08B 21/245 340/540 |
| 2010/0148971 A1 * | 6/2010 | Wawrla | E03C 1/057 340/573.1 |

(Continued)

OTHER PUBLICATIONS

International Search Report PCT/IB 2021/053026 (1 page, Aug. 20, 2021).

*Primary Examiner* — An T Nguyen
(74) *Attorney, Agent, or Firm* — Howard University School of Law

(57) ABSTRACT

This apparatus can detect a user proximity to handwashing stations by electronic mechanism of proximity sensing with radio tags and anonymously tracking tagless users. It can also guide them through proper approved hand washing hygiene steps through visual/auditory cues, can track Users time/proximity in following hand hygiene guidance, and can communicate User handwashing data to a remote database from which data can be accessed.

8 Claims, 7 Drawing Sheets

(56) References Cited

U.S. PATENT DOCUMENTS

| | | | |
|---|---|---|---|
| 2011/0206378 A1* | 8/2011 | Bolling | G08B 21/245 398/108 |
| 2011/0291841 A1* | 12/2011 | Hollock | G08B 21/245 340/573.1 |
| 2012/0212344 A1* | 8/2012 | Forsberg | G08B 5/36 340/573.1 |
| 2013/0187779 A1 | 7/2013 | Pokrajac | |
| 2013/0229276 A1* | 9/2013 | Hunter | G08B 21/245 340/501 |
| 2014/0327545 A1* | 11/2014 | Bolling | G08B 21/245 340/573.1 |
| 2015/0170502 A1* | 6/2015 | Harris | G08B 21/245 340/573.1 |
| 2015/0194043 A1* | 7/2015 | Dunn | G08B 21/245 340/573.1 |
| 2017/0256155 A1* | 9/2017 | Sengstaken, Jr. | G06K 19/0723 |
| 2017/0287313 A1* | 10/2017 | Park | A61B 5/002 |
| 2018/0047277 A1* | 2/2018 | Thyroff | G08B 21/24 |
| 2018/0151054 A1* | 5/2018 | Pi | G08B 21/245 |
| 2018/0293873 A1* | 10/2018 | Liu | G06K 7/10366 |
| 2019/0012898 A1* | 1/2019 | Wittrup | G08B 21/245 |
| 2019/0043337 A1* | 2/2019 | Liu | G16H 40/20 |
| 2019/0295548 A1* | 9/2019 | Kanfer | G10L 15/22 |
| 2019/0384968 A1* | 12/2019 | Brown | G06F 3/013 |
| 2020/0074835 A1* | 3/2020 | Waghode | G08B 21/245 |
| 2020/0074836 A1* | 3/2020 | Kolavennu | G08B 21/0438 |
| 2020/0302775 A1* | 9/2020 | Liu | G06K 7/10366 |
| 2020/0320846 A1* | 10/2020 | Trapani | G08B 21/245 |
| 2020/0323397 A1* | 10/2020 | Simonovsky | G06K 7/10366 |
| 2021/0110700 A1* | 4/2021 | Harman | G08B 5/36 |
| 2021/0335122 A1* | 10/2021 | Mahmoud | G16H 40/63 |

\* cited by examiner

SYSTEM AND METHOD FOR HAND HYGIENE COMPLIANCE

CROSS-REFERENCE TO RELATED APPLICATIONS

This application claims the benefit of priority to U.S. Provisional App. No. 63/101,012 filed Apr. 13, 2020, the contents therein are incorporated by reference in its entirety therein.

FIELD

The present disclosure relates generally to a computer system for washing hands and hygiene and collects data from usage to be stored in a database.

BACKGROUND

The current global challenge of COVID-19 pandemic has surpassed the provincial, radical, conceptual, social, and pedagogical boundaries. According to the Center of Disease Control, COVID-19 is primarily transmitted from person-to-person through respiratory droplets. These droplets are released when someone with COVID-19 sneezes, coughs, or talks. Infectious droplets can land in the mouths or noses of people who are nearby or possibly be inhaled into the lungs. A physical distance of at least 1 meter (3 ft) between persons is suggested by the World Health Organization (WHO) to avoid infection, although some WHO member states have recommended maintaining greater distances whenever possible. Respiratory droplets can land on hands, objects or surfaces around the person when they cough or talk, and people can then become infected with COVID-19 from touching hands, objects or surfaces with droplets and then touching their eyes, nose, or mouth. Recent data suggest that there can be transmission of COVID-19 through droplets of those with mild symptoms or those who do not feel ill. Short-range inhalation of aerosols is a possibility for COVID-19, as with many respiratory pathogens. However, this cannot easily be distinguished from "droplet" transmission based on epidemiologic patterns. Short-range transmission is a possibility particularly in crowded medical wards and inadequately ventilated spaces. Certain procedures in health facilities can generate fine aerosols and should be avoided whenever possible.

COVID-19 has a mean incubation period of 5.2 days. The infection is acute without any carrier status. Symptoms usually begin with nonspecific syndromes, including fever, dry cough, and fatigue. Multiple systems may be involved, including respiratory (cough, short of breath, sore throat, rhinorrhea, hemoptysis, and chest pain), gastrointestinal (diarrhea, nausea, and vomiting), musculoskeletal (muscle ache), and neurologic (headache or confusion). More common signs and symptoms are fever, cough and short of breath. There were about 15% with fever, cough, and short of breath. Hand hygiene is a part of daily institutional procedures. This includes but is not limited to clinics, restaurants, cafeterias, schools, pharmacies, and even the home. Although some individuals follow hand washing procedures, it has been found that most individuals do not.

SUMMARY

The following summary merely presents some concepts of the disclosure in a simplified form as a prelude to the more detailed description provided below. Aspects of the present disclosure relates to the encouragement of hand hygiene compliance within a concise package using radio-frequency identification tags (radio tags), anonymous tracking using a proximity sensor and provides a data connection to a database & management reporting dashboard that is accessible from anywhere.

In one aspect, a system for hand hygiene compliance may include a proximity sensor configured for sensing a presence of a human body within a predetermined radius of detection. The system may include a wireless transceiver configured communicating computer readable data representative of a state of hand washing pertaining to at least one hand of the human body based on the proximity sensor state of presence of the human body and electrically receiving RFID tag data associated with the human body. A computer processor may be configured for receiving and processing the computer readable data representative of a state of hand washing to output a hand wash state; and a visual feedback device configured for indicating said hand wash state.

In one aspect, a system for hygiene compliance may include a wireless transceiver for identifying the registered user's radio tag, a proximity sensor that can identify that a person is at a wash station without a radio tag, a form of feedback for the user to encourage proper hand hygiene procedures, and a wireless transceiver for communication over local Wi-Fi to access/update a washing status database.

In one aspect of the present disclosure, the real time washer's feedback may be a series visual and/or auditory wash progress indicators as well as including indication of successful completion of hand hygiene procedures. The user feedback may be enhanced with more "fun" music-based washing-theme songs as well as tactile feedback. These forms of feedback add the "fun" aspect to an otherwise boring set of procedures.

In one aspect of the present disclosure, the radio tags may be a small, wearable tag/sticker/band with embedded circuitry to communicate location with the Base Unit within the wash-zone area (the sink). Enhanced forms also could record and communicate proximity (distance) data to also capture "entry-zone" and other movement data as well (e.g., employees detected entering the bathroom or "entry zone" but not entering the "washing-zone" or completing the hand washing routine).

In one aspect of the present disclosure, the handwasher database may be an Internet cloud based database that keeps track of all user radio (user) data as gathered from the Base Units. This database could likewise be accessible for recording or reporting on handwashing data from virtually anywhere via various Internet connection means. Modified implementations of the database could be on a physically local server that serves the local network without relying on an Internet connected cloud-based database (e.g. as might be desired in remote or isolated locations).

BRIEF DESCRIPTION OF DRAWINGS

A more complete understanding of aspects of the present disclosure and the advantages thereof may be acquired by referring to the following description in consideration of the accompanying drawings, in which like reference numbers indicate like features, and wherein.

DETAILED DESCRIPTION

Figure 1:
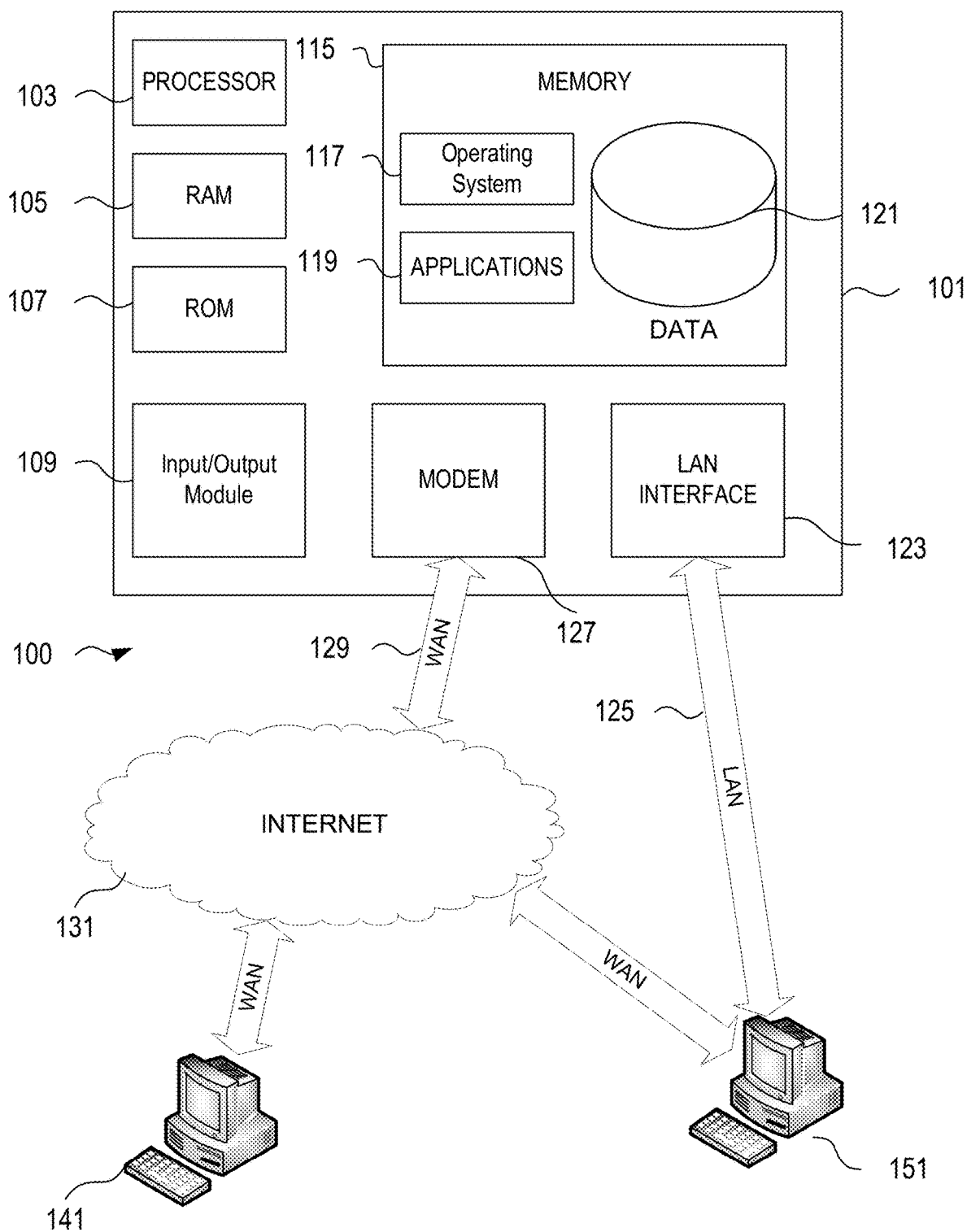
FIG. 1 illustrates a schematic diagram of a digital computing environment in which certain aspects of the present disclosure may be implemented.

The accompanying drawings, which form a part hereof, show examples of the disclosure. It is to be understood that the examples shown in the drawings and/or discussed herein are non-exclusive and that there are other examples of how the disclosure may be practiced.

FIG. 1 illustrates a block diagram of a specific programmed computing device 101 (e.g., a computer server or cloud computing environment) that may be used according to an illustrative implementation of the present disclosure. The computer server 101 may have a processor 103 for controlling overall operation of the server and its associated components, including RAM 105, ROM 107, input/output module 109, and memory 115.

Input/Output (I/O) 109 may include a microphone, keypad, touch screen, camera, and/or stylus through which a user of device 101 may provide input, and may also include one or more of a speaker for providing audio output and a video display device for providing textual, audiovisual and/or graphical output. Other I/O devices through which a user and/or other device may provide input to device 101 also may be included. Software may be stored within memory 115 and/or storage to provide computer readable instructions to processor 103 for enabling server 101 to perform various technologic functions. For example, memory 115 may store software used by the server 101, such as an operating system 117, application programs 119, and an associated database 121. Alternatively, some or all of server 101 computer executable instructions may be embodied in hardware or firmware (not shown). As described in detail below, the database 121 may provide centralized storage of characteristics associated with vendors and patrons, allowing functional interoperability between different elements located at multiple physical locations.

The server 101 may operate in a networked environment supporting connections to one or more remote computers, such as terminals 141 and 151. The terminals 141 and 151 may be personal computers or servers that include many or all of the elements described above relative to the server 101. The network connections depicted in FIG. 1 include a local area network (LAN) 125 and a wide area network (WAN) 129, but may also include other networks. When used in a LAN networking environment, the computer 101 is connected to the LAN 125 through a network interface or adapter 123. When used in a WAN networking environment, the server 101 may include a modem 127 or other means for establishing communications over the WAN 129, such as the Internet 131. It will be appreciated that the network connections shown are illustrative and other means of establishing a communications link between the computers may be used. The existence of any of various protocols such as TCP/IP, Ethernet, FTP, HTTP and the like is presumed. The network connections may be provided according to any desired encoding and modulating scheme, including Bluetooth, ZIGBEE, Z-Wave, cellular, radio frequency, WIFI, near field communications (NFC) and the like.

Computing device 101 and/or terminals 141 or 151 may also be mobile terminals including various other components, such as a battery, speaker, and antennas (not shown).

The disclosure is operational with numerous other special purpose computing system environments or configurations. Examples of computing systems, environments, and/or configurations that may be suitable for use with the disclosure include, but are not limited to, personal computers, server computers, hand-held or laptop devices, multiprocessor systems, microprocessor-based systems, cloud-based systems, set top boxes, programmable consumer electronics, network PCs, minicomputers, mainframe computers, mobile computing devices, e.g., smart phones, wearable computing devices, tablets, distributed computing environments that include any of the above systems or devices, and the like.

Database storage 121 may comprise non-transitory storage media that electronically stores information. The electronic storage media of electronic storage 121 may include one or both of system storage that is provided integrally (i.e., substantially non-removable) with computing platform 101 and/or removable storage that is removably connectable to computing platform(s) 101 via, for example, a port (e.g., a USB port, a firewire port, etc.) or a drive (e.g., a disk drive, etc.). Database storage 121 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Database storage 121 may include one or more virtual storage resources (e.g., cloud storage, a virtual private network, and/or other virtual storage resources). Database storage 121 may store software algorithms, information determined by processor(s) 103, information received from computing device 101, information received from base unit 310, and/or other information that enables base unit 310 to function as described herein.

Figure 2:
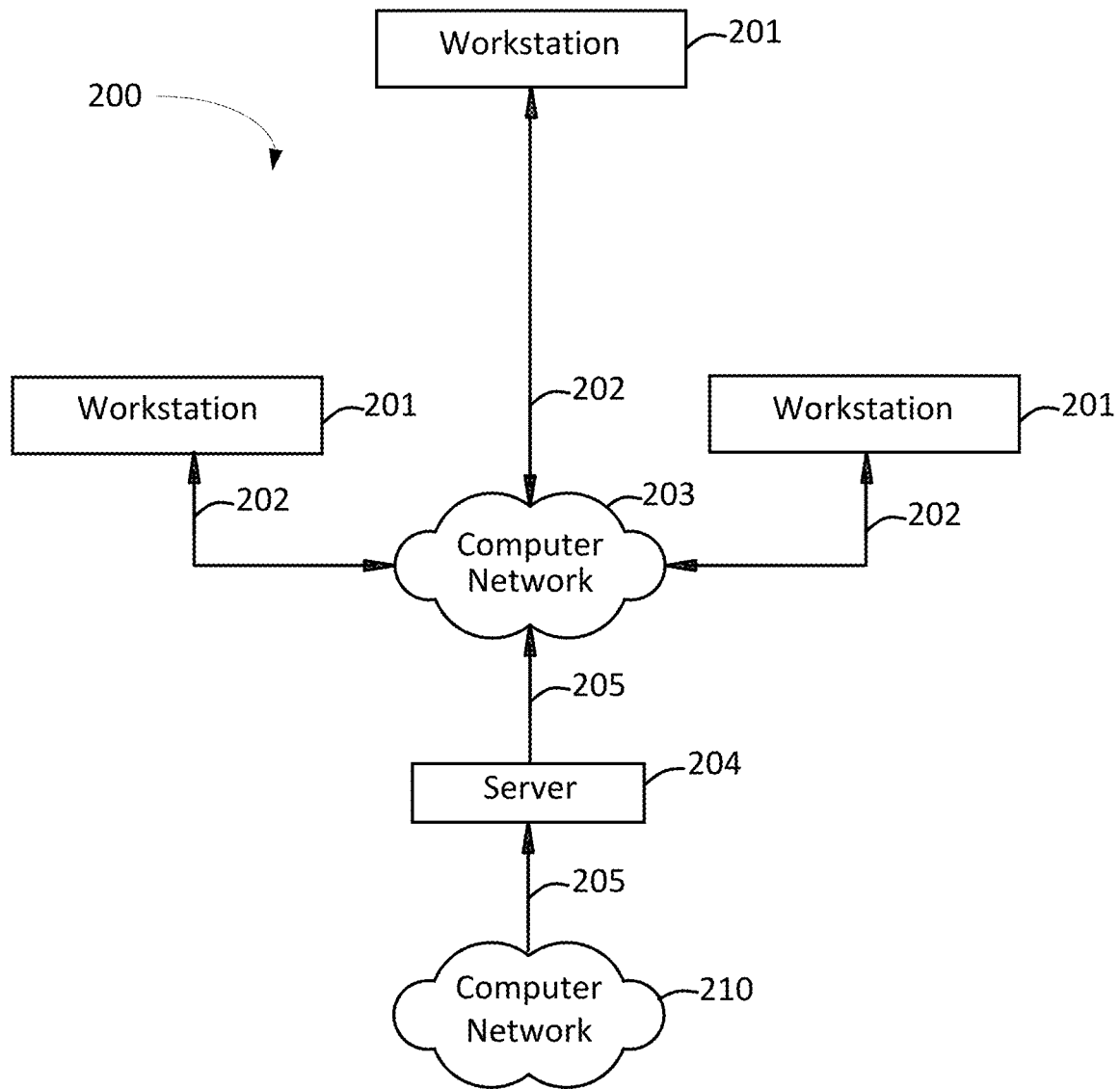
FIG. 2 is an illustrative block diagram of workstations and servers that may be used to implement the processes and functions of certain implementations of the present disclosure.

Referring to FIG. 2, an illustrative system 200 for implementing methods according to the present disclosure is shown. As illustrated, system 200 may include one or more mobile workstations 201. Mobile workstations 201 may be local or remote, and are connected by one or more communications links 202 to computer networks 203, 210 that is linked via communications links 205 to server 204. In system 200, server 204 may be any suitable server, processor, computer, or data processing device, or combination of the same. Computer network 203 may be any suitable computer network including the Internet, an intranet, a wide-area network (WAN), a local-area network (LAN), a wireless network, a digital subscriber line (DSL) network, a frame relay network, an asynchronous transfer mode (ATM) network, a virtual private network (VPN), or any combination of any of the same. Communications links 202 and 205 may be any communications links suitable for communicating between workstations 201 and server 204, such as network links, dial-up links, wireless links, hard-wired links, etc.

The disclosure may be described in the context of cloud-based computing architecture employing Amazon Web Service (AWS). Nevertheless, other commercially available cloud-based services may be used, such as Microsoft Azure, and Google Cloud. The system 300 API components may be provided in the AWS cloud and have been architected to scale in a resilient manner through the use of technologies chosen without any legacy dependencies.

The disclosure may be described in the context of computer-executable instructions, such as program modules, being executed by a computer. Generally, program modules include routines, programs, objects, components, data structures, etc. that perform particular tasks or implement particular computer data types. The disclosure may also be practiced in distributed computing environments where tasks are performed by remote processing devices that are linked through a communications network. In a distributed computing environment, program modules may be located in both local and remote computer storage media including memory storage devices.

FIGS. 3-7 illustrates schematic diagrams of a system environment 300 that may be used according one or more illustrative implementations of the present disclosure. The system 300 includes a Base Unit 310 that may be mounted on a wall over a hand washing station 320. Base Unit 310 relays/transmits collected computer readable data via WIFI network 303 to a cloud-based computing architecture 325 having a cloud-based database 330 which stores the data from the Base Unit 310. In use, a User 400 becomes within range of the Base Unit 310 by way of a radio tag 340 (e.g., RFID badge) worn by the User 400 to track hand hygiene compliance.

Figure 3:
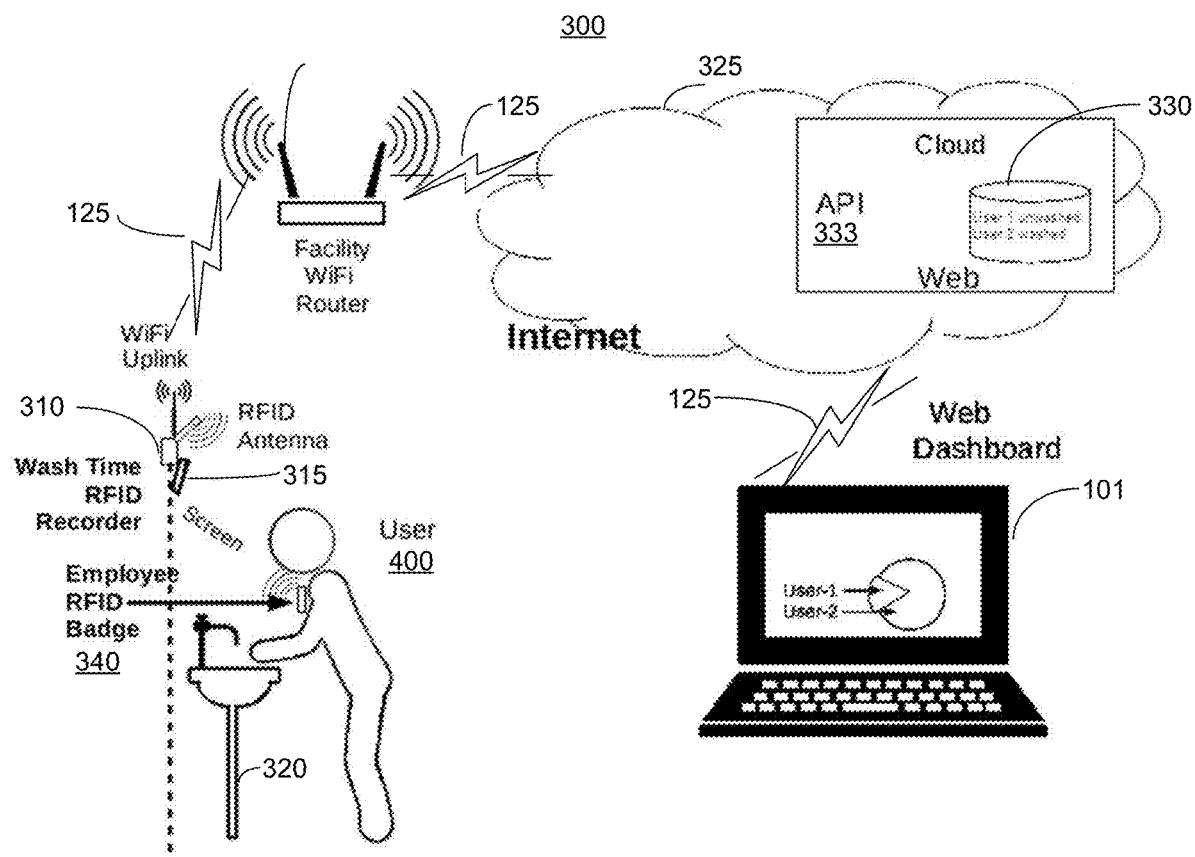
FIG. 3 illustrates a schematic representation of a system may be used to implement the processes and functions of certain implementations of the present disclosure.
Figure 4:
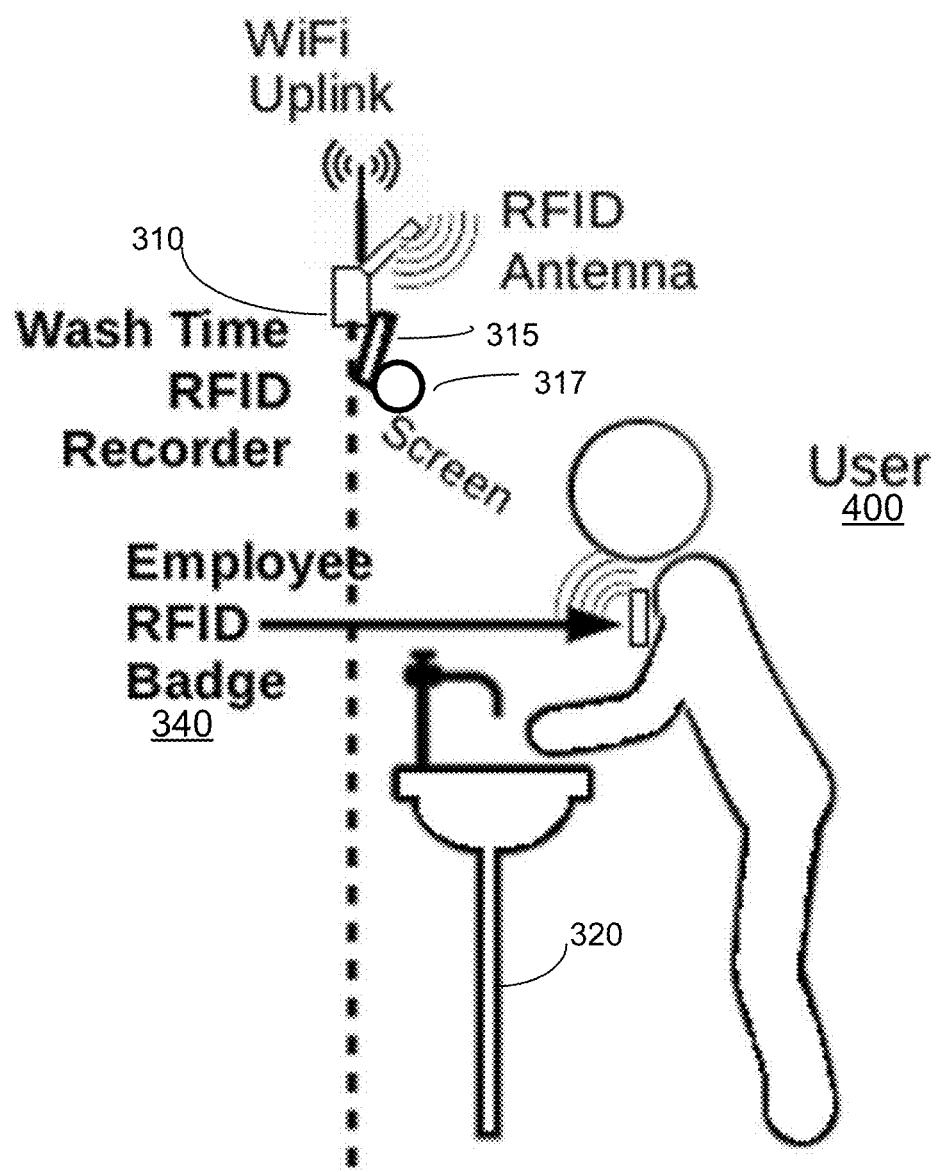
FIG. 4 illustrates a schematic representation of a system may be used to implement the processes and functions of certain implementations of the present disclosure.
Figure 5:
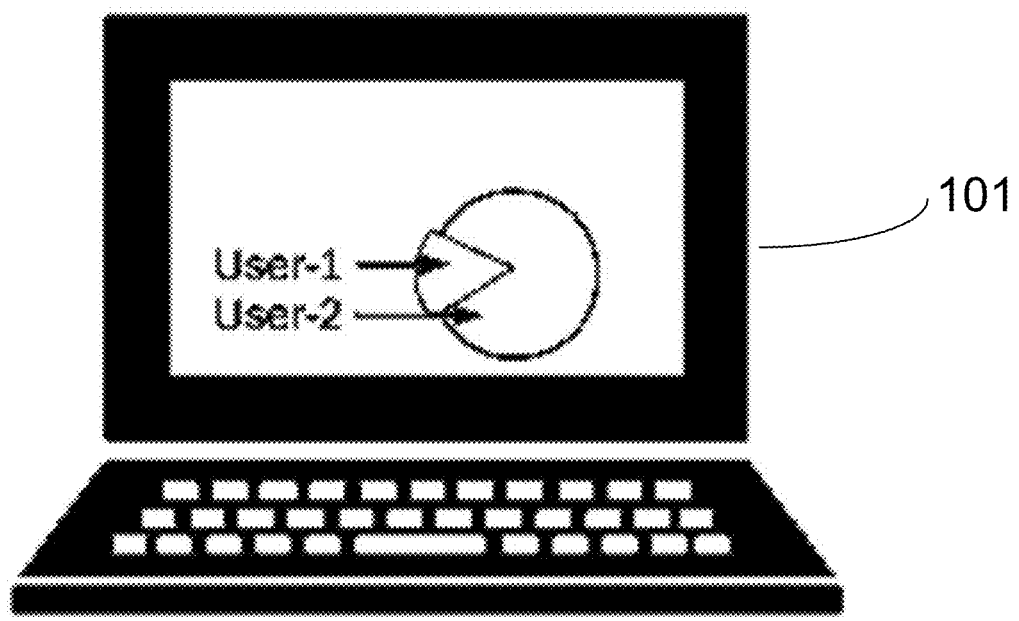
FIG. 5 illustrates a schematic representation of a system may be used to implement the processes and functions of certain implementations of the present disclosure.

FIGS. 3 and 4 illustrates a User 400 at a hand washing station 320 whose radio tag 340 was sensed by the Base Unit 310 which then relays the User's 400 hand washing compliance computer readable data to the cloud application program 333. The cloud application program 333 records the compliance data to database 330 which can then be accessed via a variety of devices, such as a web-connected computing device 101, such as a laptop.

In some implementations, the Base Unit 310 comprises a transceiver and proximity sensor 317 that can detect a User's radio tag 340, and track users who have no tag. The transceiver that can communicate with the web 325 to access the cloud application 333 and some form of feedback for the User 400, such as the screen 315 illustrated in FIG. 6. This feedback could include but not limited to identifying the User name, showing a time-based progress bar and prompts for procedural steps.

In some implementations, the Base Unit 310 transceiver type could be adapted for each institution appropriate wireless configuration. In one configuration, it could be WIFI for connecting to the web-based cloud database 330. In another configuration, it could be changed to other current forms of transmission protocols, such as mesh networks, or future protocols, transceivers, and frequencies as the industries & capabilities expand. The network connections may be provided according to any desired encoding and modulating scheme, including Bluetooth, ZIGBEE, Z-Wave, cellular, radio frequency, WIFI, near field communications (NFC) and the like.

Likewise, the Base Unit's 310 transceiver method for communicating with the User radio tag 340 may not be limited to one type of wireless transmission or one type of radio tag 340. These could be passive or active radio tags architecture. The architecture could use HF (13.56 MHz), UHG (700-900 MHz) or Bluetooth (2.4 GHz) frequencies and various protocols. They could use a number of current or future protocols or frequencies as the industry develops and as governing bodies regulate frequencies.

In some implementations, the radio tags 340 could take a number of different wearable forms. Tags 340 could be tags, badges, wristbands, pins, stickers and/or labels. They could be integrated into other wearable technology such as smart watches, phones, or sportswear. In one construction Base Unit 310 could be set up to use sense another wearable device that is normally used for something else (such as a phone or sports tracker) in place of a dedicated radio tag 340. The radio tag 340 could be incorporated into the institution's employee identification or time-tracking systems.

In some implementations, the Base Unit 310 could also contain a proximity sensor 317 in some implementations. The proximity sensor 317 may be configured for sensing a presence of a human body within a predetermined radius of detection. The proximity sensor 317 would be able to record anonymous users when no known RFID tag 340 is present, but a person is sensed in front of the Base Unit 310. This proximity sensor 317 may include an ultrasonic, infrared, or motion sensor. The collected data from the proximity sensor 317 could be compiled and reported to the cloud application program 333. The cloud application program 333 would record the anonymous user data to its database 330 which could then be accessed via a web device 101 to analyze and present the anonymous data. In some implementations, the Base Unit 310 could also simultaneously use both RF identified for the User 400 and anonymous tracking.

Figure 6:
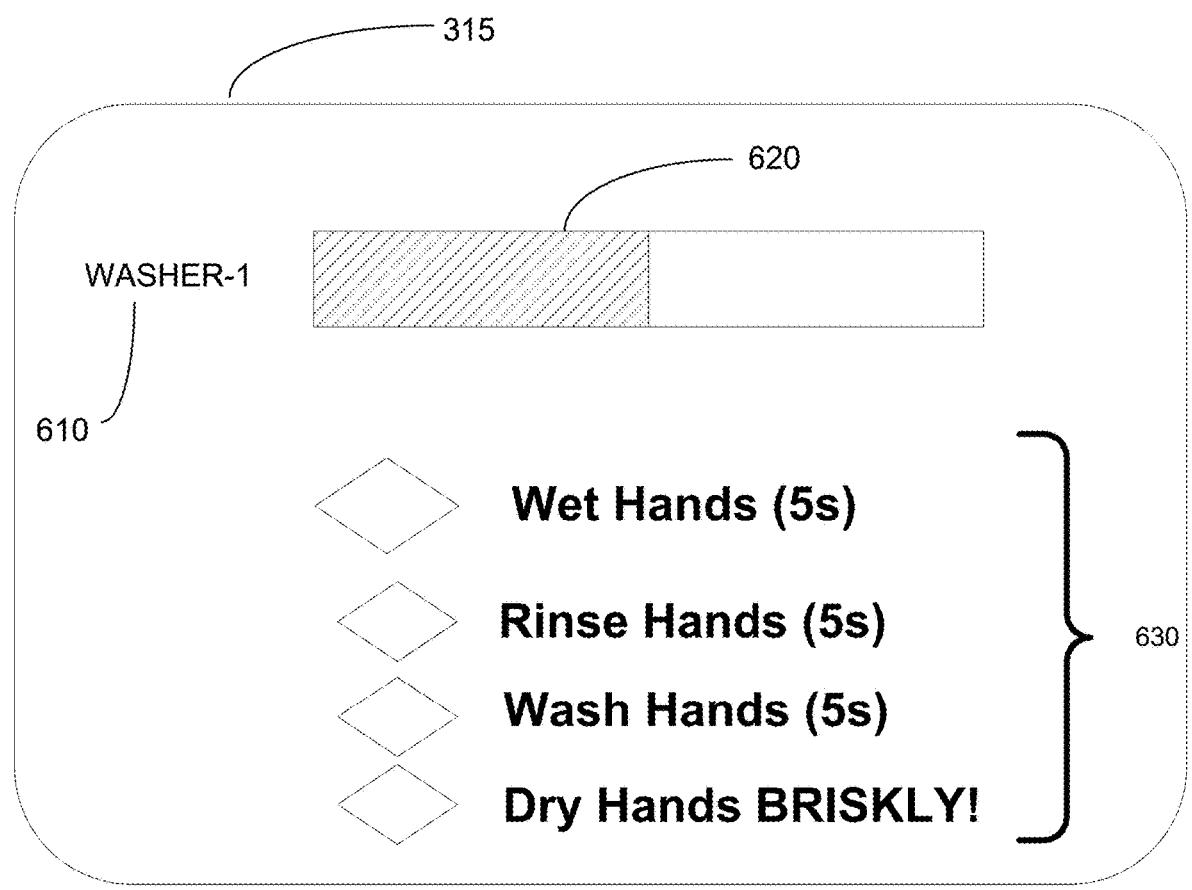
FIG. 6 shows an example visual feedback on the Base Unit to implement the processes and functions of certain implementations of the present disclosure.

In some implementations, the feedback signal from Base Unit 310 can take many different forms and is designed to encourage the User to comply with particularly the time-based aspects of the institution's hand hygiene practices. A visual feedback signal could be displayed on a screen 315 as illustrated in the present disclosure as seen in FIG. 6. The visual feedback signal could as well be a series of LED light sequences that mark the timed progress of the User presence at the hand washing station. The visual feedback signal could show progress bars 8, User identification 7, procedural prompts 8 and other forms of encouragement/prompts. These graphical user feedback of a display screen 315 may include but are not limited to circular progress bars, patterns, animated characters, visual illustrations of the steps and changing colors.

In some implementations, the Base Unit 310 may use an auditory feedback signal in conjunction with visual feedback signal or on its own. The auditory feedback signal could include a series of beeps or music or verbal cues and encouragement. Auditory feedback would be especially appropriate for encouraging/prompting visually impaired individuals. In some implementations, The Base Unit 310 could use other forms of feedback such as tactile feedback or haptic feedback. This could take the form of a vibration, or braille points.

The database 330 in its preferred implementation may be a cloud-based database and management reporting dashboard accessible via the Internet 131. This could be managed by the institution or by a third party. In some implementations, the database 330 could be a local based server physically located on the premises of the institution. This would be most appropriate when there is limited, restricted or no internet connectivity outside the institution. This could include cruise ships, remote clinics, or military institutions with restricted/protected connectivity with the outside.

In some implementations, the database 330 may be designed for access by other physical devices 101 such as smartphones, laptops, and computers. This would allow supervisors to check for hand hygiene compliance at any time. This could be used to support health inspections, employee managers, wash hygiene compliance certification auditors, provide employee incentives and produce progress reports.

In some implementations, a proximity sensor 317 that can identify that "someone" is at the wash station—even if the unit cannot identify who is at the wash station (no RF tag 340 present). This feature arose from the need to encourage children in a school environment to wash their hands in the bathrooms. With the proximity sensor 317 in Base Unit 310, the unit can still trigger its handwash-prompting cycle for the anonymous user. It can also still upload the successful time spent at the wash station (or lack thereof) to the cloud for the anonymous hand washer. Thus, schools could see if certain classes (based on what time periods and which bathrooms were used) need more training in proper handwashing. Even competitions between different classes/grades could be staged. The optional usage of a proximity sensor 317 in some models could be, but not limited to, ultrasonic, infrared, or motion sensors.

In some implementations, the collection, compilation and reporting capability of the cloud-based backend 330 to analyze and present the anonymous data. In some implementations, the simultaneous usage of both RF identified and anonymous tracking in a single unit. In some implementations, so the unit could identify and record an RF identified user (such as a teacher) when present, or record an anonymous user when no known RFD is present, but a person is sensed. In some implementations, a timed progress bar is shown indicating elapsed time through the hand washing procedure.

In some implementations referring to FIG. 6, a visual cue may indicate what to do in order to comply with hand hygiene procedures. Screen 315 shows the User's identification 610. In a further implementation, a timed progress bar 620 indicates elapsed time through the hand washing procedure. Further on screen 315, a visual cue of 630 steps as to what to be doing to comply with hand hygiene procedures.

Figure 7:
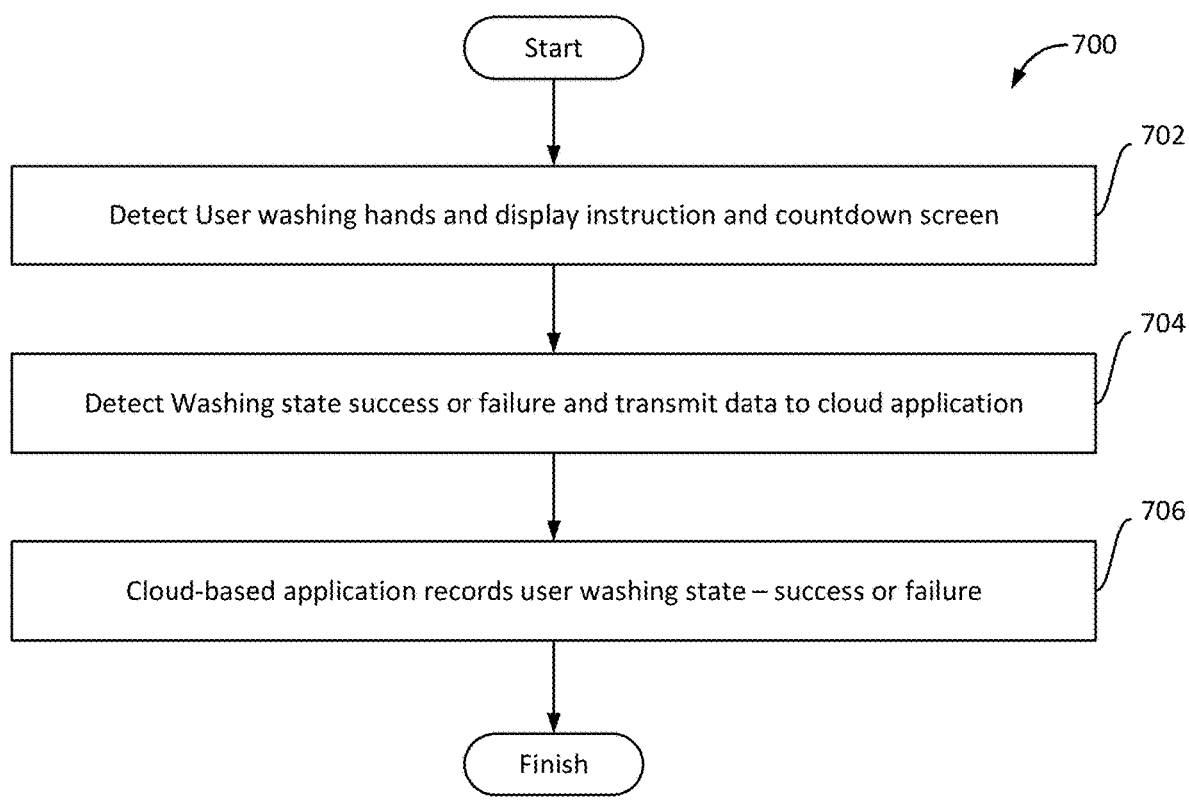
FIG. 7 illustrates a method for data communication in accordance with one or more implementations.

FIG. 7 illustrates a method 700 for data processing, in accordance with one or more implementations. The operations of method 700 presented below are intended to be illustrative. In some implementations, method 700 may be accomplished with one or more additional operations not described, and/or without one or more of the operations discussed. Additionally, the order in which the operations of method 700 are illustrated in FIG. 7, and described below is not intended to be limiting.

In some implementations, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

FIG. 7 illustrates method 700, in accordance with one or more implementations. An operation 702 may include electronically detecting user 400 washing hands and displaying instructions as showing in FIG. 6 and countdown screen. Operation 702 may be performed by one or more hardware processors configured by machine-readable instructions including software module in accordance with one or more implementations.

An operation 704 may include electronically detecting a washing state success or failure based on compliance instructions and computer data is transmitted to the cloud application 333 and stored in database 330. Operation 704 may be performed by one or more hardware processors configured by machine-readable instructions including software module in accordance with one or more implementations.

An operation 706 may include electronically processing the data and in cloud-based application to record washing state. Operation 706 may be performed by one or more hardware processors configured by machine-readable instructions including software module in accordance with one or more implementations.

In addition, it should be understood that the figures and algorithms, which highlight the functionality and advantages of the present disclosure, are presented for example purposes only. The architecture of the present disclosure is sufficiently flexible and configurable, such that it may be utilized in ways other than that shown in the accompanying figures and algorithms. For example, the steps listed in any flowchart may be re-ordered or only optionally used in some embodiments.

It should be noted the terms "including" and "comprising" should be interpreted as meaning "including, but not limited to".

In this specification, "a" and "an" and similar phrases are to be interpreted as "at least one" and "one or more." References to "the," "said," and similar phrases should be interpreted as "the at least one", "said at least one", etc. References to "an" embodiment in this disclosure are not necessarily to the same embodiment.

It is the applicant's intent that only claims that include the express language "means for" or "step for" be interpreted under 35 U.S.C. 112. Claims that do not expressly include the phrase "means for" or "step for" are not to be interpreted under 35 U.S.C. 112.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

While illustrative systems and methods as described herein embodying various aspects of the present disclosure are shown, it will be understood by those skilled in the art, that the disclosure is not limited to these implementations. Modifications may be made by those skilled in the art, particularly in light of the foregoing teachings. For example, each of the elements of the aforementioned implementations may be utilized alone or in combination or sub-combination with elements of the other implementations. It will also be appreciated and understood that modifications may be made without departing from the true spirit and scope of the present disclosure. The description is thus to be regarded as illustrative instead of restrictive on the present disclosure.

What is claimed is:

1. A system for hand hygiene compliance, comprising:
  a proximity sensor configured for sensing a state of presence or non-presence of a human body within a first predetermined radius of detection defined as a washing-zone;

a wireless transceiver configured for communicating computer readable data representative of a state of hand washing pertaining to at least one hand of the human body based on the proximity sensor state of presence of the human body in said washing zone and electrically receiving RFID tag data associated with the human body;

a processor configured for receiving and processing the computer readable data representative of a state of hand washing to output a hand wash state; wherein the processor is configured for braille point feedback of said hand washing state; and a visual feedback device configured for displaying said hand wash state.

2. The system of claim 1, wherein said proximity sensor is selected from a group comprising one or more of an ultrasonic sensor, an infrared sensor, and a motion sensor.

3. The system of claim 1, wherein said transceiver is selected from a group comprising one or more WIFI, Zigbee, and a Mesh Network.

4. The system of claim 1, wherein said transceiver is configured for a method of communication with the RFID tag data is transmitted in a group selected from one or more of HF (13.56 MHz), UHG (700-900 MHz) and Bluetooth (2.4 GHz).

5. The system of claim 1, further comprising a cloud-based data collection system configured for recording said hand wash state.

6. The system of claim 5, wherein said wireless transceiver transmits said hand wash state to said data collection system.

7. The system of claim 1, wherein said transceiver further comprises a data collection system, said data collection system being configured for recording said hand wash state.

8. The system of claim 1, wherein said visual feedback device is configured for displaying a user identification graphical object, a timer graphical object, and a plurality of hand hygiene compliance graphical object cues.

* * * * *